US012286664B2

(12) United States Patent
Lacarte et al.

(10) Patent No.: US 12,286,664 B2
(45) Date of Patent: Apr. 29, 2025

(54) PIPE WEIGHT COATING

(71) Applicant: BASF SE, Ludwigsahfen am Rhein (DE)

(72) Inventors: Chris Lacarte, Toronto (CA); Staci L. Wegener, Wyandotte, MI (US); Jian Ying Zang, Toronto (CA); Lyle Caillouette, Wyandotte, MI (US)

(73) Assignee: BASF SE, Ludwigshafen am Rhein (DE)

( * ) Notice: Subject to any disclaimer, the term of this patent is extended or adjusted under 35 U.S.C. 154(b) by 673 days.

(21) Appl. No.: 17/606,616

(22) PCT Filed: Apr. 30, 2020

(86) PCT No.: PCT/US2020/030593
§ 371 (c)(1),
(2) Date: Oct. 26, 2021

(87) PCT Pub. No.: WO2020/223424
PCT Pub. Date: Nov. 5, 2020

(65) Prior Publication Data
US 2022/0235244 A1    Jul. 28, 2022

Related U.S. Application Data

(60) Provisional application No. 62/840,667, filed on Apr. 30, 2019.

(51) Int. Cl.
C09D 175/08 (2006.01)
C12Q 1/06 (2006.01)

(52) U.S. Cl.
CPC ............ C12Q 1/06 (2013.01); C09D 175/08 (2013.01)

(58) Field of Classification Search
CPC .................................................. C09D 175/08
USPC ......................................................... 524/590
See application file for complete search history.

(56) References Cited

U.S. PATENT DOCUMENTS

| | | | | |
|---|---|---|---|---|
| 4,395,159 A * | 7/1983 | Karuks | ................... | F16L 58/06 427/403 |
| 8,944,114 B2 * | 2/2015 | Mueller | ................... | F16L 58/06 138/146 |
| 10,371,307 B2 * | 8/2019 | Nederlof | ................ | C09D 5/084 |
| 2012/0315095 A1 * | 12/2012 | Mueller | ............. | F16L 58/1063 427/403 |
| 2013/0022810 A1 | 1/2013 | Bower et al. | | |
| 2016/0252205 A1 * | 9/2016 | Nederlof | .................. | C09D 5/00 138/145 |
| 2016/0272845 A1 * | 9/2016 | Shen | .................... | C09D 175/04 |

FOREIGN PATENT DOCUMENTS

| | | | | |
|---|---|---|---|---|
| WO | 82/03438 A1 | 10/1982 | | |
| WO | 92/06083 | 4/1992 | | |
| WO | WO-2011084793 A1 * | 7/2011 | ............. | C03C 12/00 |
| WO | 2015/155277 A1 | 10/2015 | | |
| WO | 2016/133758 A1 | 8/2016 | | |
| WO | WO-2018052904 A1 * | 3/2018 | ......... | C04B 20/1022 |

OTHER PUBLICATIONS

International Preliminary Report on Patentability from corresponding International Application No. PCT/US2020/030593 dated Nov. 11, 2021.
Translation of Brazilian Search Report and Written Opinion dated Sep. 13, 2023, in Brazilian Application No. 112021021380-5, 4 pages.
First Office Action from corresponding Chinese Patent Application No. 202080028322 dated Jun. 17, 2022, and its English translation.
International Search Report and Written Opinion from corresponding International Application No. PCT/US2020/030593 dated Aug. 25, 2020.
Office Action issued in Brazilian Patent Application No. 112021021380-5, on Dec. 10, 2024, 7 pages with English translation.

* cited by examiner

*Primary Examiner* — Deve V Hall
(74) *Attorney, Agent, or Firm* — Grüneberg and Myers PLLC

(57) ABSTRACT

Provided herein are novel and improved weight coating systems suitable for use with pipes, particularly pipes that are submerged in liquid, such as water, in environments including oceans, seas, marshes, lakes and rivers. The novel coating systems provided herein comprise an aggregate and a polyurethane binder, wherein the polyurethane binder is a two-component composition comprising an isocyanate component and an iso-cyanate-reactive component. The coating systems provided have increased durability, as well as flexibility allowing for efficiencies related to transportation, storage, use and resistance to corrosive effects. Furthermore, the coating systems are cost effective and have minimal or zero impact on the environments in which they are utilized.

20 Claims, 2 Drawing Sheets

PIPE WEIGHT COATING

FIELD OF THE INVENTION

The present disclosure generally relates to a pipe weight coating system comprising a weight coating disposed around a pipe, wherein the coating comprises an aggregate and a polyurethane binder, and wherein the polyurethane binder is a two-component composition comprising an isocyanate component and an isocyanate-reactive component.

DESCRIPTION OF THE RELATED ART

The present disclosure generally relates to subsea pipe lines for oil and gas applications. Such pipe lines conventionally use a concrete weight coating around the pipe to ensure that pipes laid offshore, e.g., wetlands, marshland, bodies of water, have a negative buoyancy as oil and gas are lighter than water. Thus, the weight coating provides a weighting function.

Although several types of conventional weight coatings are currently available, they are suboptimal for a variety of reasons. For example, in certain products, concrete used for the conventional weight coating requires at least 28 days to cure before it can be placed into use, hindering production capability and introducing an array of inefficiencies. A further problem with conventional weight coatings is that concrete generally lacks the flexibility to be reeled and, therefore, cannot be installed by a reel lay barge. What is required is the availability of coating materials having improved flexibility allowing for longer lengths of pipe to be produced, welded, and subsequently reeled onto large reels, thereby minimizing the amount of field work required and increasing the speed of installation. Furthermore, since concrete, generally, requires a large amount of energy to process and the final product is basic, it causes an increase in the pH of the water where it is placed; what is needed therefore, is a material that is neutral and does not disrupt pH or other chemical levels in the environment in which it is utilized.

Thus, there is a need for an improved pipe weight coating systems that can be easily produced and easily installed. Ideally, such coating systems should be cost effective, energy efficient and have a neutral effect on the environment in which they are installed and used.

SUMMARY OF THE INVENTION

The present disclosure is directed to pipe weight coating systems comprising a weighted coating disposed around a pipe, wherein the coating comprises an aggregate and a polyurethane binder, and wherein the polyurethane binder is a two-component composition comprising an isocyanate component and an isocyanate-reactive component. The present disclosure is further directed to a method for producing the weight coating system, comprising: providing the isocyanate component and the isocyanate-reactive component; mixing the isocyanate component and the isocyanate-reactive component to form the polyurethane binder; applying the polyurethane binder to the aggregate to form the weight coating; and applying the weight coating onto the pipe.

Pipe weight coating systems provided in the present disclosure utilize a polyurethane binder with aggregate that can cure and be shipped within 24 hours. The flexibility of the polyurethane binder allows for longer lengths of pipe to be produced, welded, and subsequently reeled onto large reels, thereby minimizing the amount of field work required and increasing the speed of installation.

DETAILED DESCRIPTION

A pipe weight coating system and a method for producing the pipe weight coating system are described herein. The resulting pipe weight coating system can be used for various applications, such as oil and gas pipeline applications.

Figure 1:
FIG. 1 shows a front perspective of an exemplary weight coating system.
Figure 2:
FIG. 2 shows a cross section view of an exemplary weight coating system.
Figure 3:
FIG. 3 shows an above perspective of an exemplary weight coating system.

In embodiments, a pipe weight coating system is provided comprising: a pipe and a weight coating disposed around the pipe comprising an aggregate and a polyurethane binder, wherein the polyurethane binder is a two-component composition comprising an isocyanate component and an isocyanate-reactive component. FIGS. 1-3 provide a front perspective, a cross section view, and an above perspective of an exemplary weight coating system.

The binder comprises an isocyanate component and an isocyanate-reactive component. In certain embodiments, the isocyanate component comprises a polymeric isocyanate, and optionally, an isocyanate-prepolymer. In other embodiments, the isocyanate component comprises the polymeric isocyanate and the isocyanate-prepolymer. The isocyanate-reactive component comprises a hydrophobic polyol and, optionally, a chain extender. Typically, the system is provided in two or more discrete components, such as the isocyanate component and the isocyanate-reactive (or resin) component, i.e., as a two-component (or 2K) system, which is described further below.

It is to be appreciated that reference to the isocyanate and resin components, as used herein, is merely for purposes of establishing a point of reference for placement of the individual components of the system, and for establishing a parts by weight basis. As such, it should not be construed as limiting the present disclosure to only a 2K system. For example, the individual components of the system can all be kept distinct from each other. The terminology "isocyanate-reactive" component and "resin" component is interchangeable in the description of the present disclosure.

The binder may also comprise additional components, which may be included with either one or both of the isocyanate and resin components, or completely distinct, such as in a third component, as described further below. In certain embodiments, the binder is the reaction product of the isocyanate and isocyanate-reactive components. The binder is described further below.

If employed, the isocyanate-prepolymer is generally the reaction product of an isocyanate and a polyol and/or a polyamine, typically the reaction product of an isocyanate and a polyol. The isocyanate-prepolymer can be formed by various methods understood by those skilled in the art or can be obtained commercially from a manufacturer, a supplier, etc.

With regard to the isocyanate used to form the isocyanate-prepolymer, the isocyanate includes one or more isocyanate (NCO) functional groups, typically at least two NCO functional groups. Suitable isocyanates, for purposes of the present disclosure include, but are not limited to, conventional aliphatic, cycloaliphatic, aryl and aromatic isocyanates. In certain embodiments, the isocyanate is selected from the group of diphenylmethane diisocyanates (MDIs), polymeric diphenylmethane diisocyanates (PMDIs), and combinations thereof. Polymeric diphenylmethane diisocyanates are also referred to in the art as polymethylene polyphenylene polyisocyanates. Examples of other suitable isocyanates, for purposes of the present disclosure include, but are not limited to, toluene diisocyanates (TDIs), hexamethylene diisocyanates (HDIs), isophorone diisocyanates (IPDIs), naphthalene diisocyanates (NDIs), and combinations thereof. Typically, the isocyanate used to form the isocyanate-prepolymer comprises diphenylmethane diisocyanate (MDI).

If employed to form the isocyanate-prepolymer, the polyol includes one or more hydroxyl (OH) functional groups, typically at least two OH functional groups. The polyol can be any type of polyol known in the art. The polyol is typically selected from the group of ethylene glycol, diethylene glycol, propylene glycol, dipropylene glycol, butanediol, glycerol, trimethylolpropane, triethanolamine, pentaerythritol, sorbitol, and combinations thereof. Other suitable polyols, for purposes of the present disclosure, are described below with description of an additional, optional, component, a supplemental polyol.

The polyol can be used in various amounts relative to the isocyanate, as long as an excess of NCO functional groups relative to OH functional groups are present prior to reaction such that the isocyanate-prepolymer, after formation, includes NCO functional groups for subsequent reaction. The isocyanate-prepolymer typically has an NCO content of from about 18 to about 28, more typically from about 20 to about 25, and yet more typically about 22.9, wt. %.

If employed to form the isocyanate-prepolymer, the polyamine includes one or more amine functional groups, typically at least two amine functional groups. The polyamine can be any type of polyamine known in the art. The polyamine is typically selected from the group of ethylene diamine, toluene diamine, diaminodiphenylmethane and polymethylene polyphenylene polyamines, aminoalcohols, and combinations thereof. Examples of suitable aminoalcohols include ethanolamine, diethanolamine, triethanolamine, and combinations thereof.

The polyamine can be used in various amounts relative to the isocyanate, as long as an excess of NCO functional groups relative to amine functional groups are present prior to reaction such that the isocyanate-prepolymer, after formation, includes NCO functional groups for subsequent reaction. The NCO content of the isocyanate-prepolymer is as described and exemplified above.

It is to be appreciated that the isocyanate-prepolymer may be formed from a combination of two or more of the aforementioned polyols and/or two or more of the aforementioned polyamines. Typically, the isocyanate-prepolymer is a reaction product of the isocyanate and at least one polyol such that the isocyanate-prepolymer includes urethane linkages and NCO functional groups after formation. In a specific embodiment of the present disclosure, the isocyanate-prepolymer comprises a blend of polymeric methyldiphenyldiisocyanate and quasi-prepolymers of 4,4'-methyldiphenyldiisocyanate. Specific examples of suitable isocyanate-prepolymers, for purposes of the present disclosure, are commercially available from BASF Corporation of Florham Park, N.J., under the trademark LUPRANATE®, such as LUPRANATE® MP102. It is to be appreciated that the system can include a combination of two or more of the aforementioned isocyanate-prepolymers.

With regard to the polymeric isocyanate, the polymeric isocyanate includes two or more NCO functional groups. The polymeric isocyanate typically has an average functionality of from about 1.5 to about 3.0, more typically from about 2.0 to about 2.8, and yet more typically about 2.7. The polymeric isocyanate typically has an NCO content of from about 30 to about 33, more typically from about 30.5 to about 32.5, and yet more typically about 31.5, wt. %.

Suitable polymeric isocyanates, for purposes of the present disclosure include, but are not limited to, the isocyanates described and exemplified above for description of the isocyanate-prepolymer. Typically, the polymeric isocyanate comprises polymeric diphenylmethane diisocyanate (PMDI).

Specific examples of suitable polymeric isocyanates, for purposes of the present disclosure, are commercially available from BASF Corporation under the trademark LUPRANATE®, such as LUPRANATE® M20 Isocyanate. It is to be appreciated that the system can include a combination of two or more of the aforementioned polymeric isocyanates.

The isocyanate-prepolymer is typically present in the isocyanate component in an amount of from about 25 to about 75, more typically from about 50 to about 75, yet more typically from about 55 to about 65, and yet even more typically about 60, parts by weight, each based on 100 parts by weight of the isocyanate component. In certain embodiments, the isocyanate-prepolymer is typically present in the system in an amount of from about 50 to about 250, more typically from about 100 to about 200, yet more typically from about 125 to about 175, and yet even more typically about 150, parts by weight, each per 100 parts by weight of the polymeric isocyanate in the system. Said another way, the isocyanate-prepolymer and the polymeric isocyanate are typically present in the system, e.g. in the isocyanate component, in a weight ratio of from about 1:2 to about 2.5:1, more typically from about 1:1 to about 2:1, yet more typically from about 1.25:1 to about 1.75:1, and yet even more typically about 1.5:1.

Without being bound or limited to any particular theory, it is believed that the combination and ratios of the isocyanate-prepolymer and the polymeric isocyanate, as described and exemplified immediately above, imparts the binder with increased tensile strength, elongation, hardness, and glass transition temperature, as well as improved tear strength relative to conventional binders.

With regard to the hydrophobic polyol, the hydrophobic polyol includes one or more OH functional groups, typically at least two OH functional groups. Hydrophobicity of the hydrophobic polyol can be determined by various methods, such as by visual inspection of the reaction product of the hydrophobic polyol with isocyanate where the reaction product has been immediately de-gassed after mixing the two components and then introduced into water, where the reaction product is allowed to cure. If there is no evidence of marring or wrinkling at the interface (or surface) between the reaction product and the water, or if there is no evidence of bubble or foam formation, hydrophobicity of the hydrophobic polyol is considered excellent.

The hydrophobic polyol typically comprises a natural oil polyol (NOP). In other words, the hydrophobic polyol is typically not a petroleum-based polyol, i.e., a polyol derived from petroleum products and/or petroleum by-products. In general, there are only a few naturally occurring vegetable oils that contain unreacted OH functional groups, and castor oil is typically the only commercially available NOP produced directly from a plant source that has sufficient OH functional group content to make castor oil suitable for direct use as a polyol in urethane chemistry. Most, if not all, other NOPs require chemical modification of the oils directly available from plants. The NOP is typically derived from any natural oil known in the art, typically derived from a vegetable or nut oil. Examples of suitable natural oils, for purposes of the present disclosure, include castor oil, and NOPs derived from soybean oil, rapeseed oil, coconut oil, peanut oil, canola oil, etc. Employing natural oils can be useful for reducing environmental footprints.

Typically, as alluded to above, the hydrophobic polyol comprises castor oil. Those skilled in the art appreciate that castor oil inherently includes OH functional groups whereas other NOPs may require one or more additional processing steps to obtain OH functional groups. Such processing steps, if necessary, are understood by those skilled in the art. Suitable grades of castor oil, for purposes of the present disclosure, are commercially available from a variety of suppliers. For example, T31® Castor Oil, from Eagle Specialty Products (ESP) Inc. of St. Louis, Mo., can be employed as the hydrophobic polyol. Specific examples of other suitable hydrophobic polyols, for purposes of the present disclosure, include polyether/polyester polyols, which are commercially available from Cognis Corporation of Cincinnati, Ohio, under the trademark SOVERMOL®, such as SOVERMOL® 750, SOVERMOL® 805, SOVERMOL® 1005, SOVERMOL® 1080, and SOVERMOL® 1102.

The hydrophobic polyol is typically present in the system in an amount of from about 80 to about 99, more typically about 85 to about 95, yet more typically from about 90 to about 95, and yet even more typically about 92.5, parts by weight, each based on 100 parts by weight of the resin component of the system. It is to be appreciated that the system can include a combination of two or more of the aforementioned hydrophobic polyols.

With regard to the chain extender, the chain extender has at least two OH functional groups. The chain extender typically has a molecular weight of from about 62 to about 220, more typically from about 62 to about 150, and yet more typically about 132. As such, the chain extender can be referred to in the art as a "short" chain extender. The chain extender typically comprises an alkylene glycol. Examples of suitable chain extenders, for purposes of the present disclosure, include dipropylene glycol (DPG), diethylene glycol (DEG), NIAX® DP-1022, 1,3-propanediol, 1,4-butanediol, 1,5-pentanediol, 1,6-hexanediol, and 2-butene-1,4-diol. In a specific embodiment, the chain extender is dipropylene glycol.

The chain extender is typically present in the system in an amount of from about 1.0 to about 20, more typically from about 5.0 to about 10, and yet more typically about 7, parts by weight, each based on 100 parts by weight of the resin component. It is to be appreciated that the system may include any combination of two or more of the aforementioned chain extenders.

Without being bound or limited to any particular theory, it is believed that the chain extender imparts increased strength to the binder, as well as increased strength, tear strength, and hardness to the binder.

In other embodiments of the present disclosure, a supplemental polyol, such as a petroleum-based polyol, may be used in addition to the hydrophobic polyol. If employed, the supplemental polyol is typically selected from the group of conventional polyols, such as ethylene glycol, diethylene glycol, propylene glycol, dipropylene glycol, butane diol, glycerol, trimethylolpropane, triethanolamine, pentaerythritol, sorbitol, and combinations thereof. Typically, the supplemental polyol is selected from the group of polyether polyols, polyester polyols, polyether/ester polyols, and combinations thereof; however, other supplemental polyols may also be employed as described further below.

Suitable polyether polyols, for purposes of the present disclosure include, but are not limited to, products obtained by the polymerization of a cyclic oxide, for example ethylene oxide (EO), propylene oxide (PO), butylene oxide (BO), or tetrahydrofuran in the presence of polyfunctional initiators. Suitable initiator compounds contain a plurality of active hydrogen atoms, and include water, butanediol, ethylene glycol, propylene glycol (PG), diethylene glycol, triethylene glycol, dipropylene glycol, ethanolamine, diethanolamine, triethanolamine, toluene diamine, diethyl toluene diamine, phenyl diamine, diphenylmethane diamine, ethylene diamine, cyclohexane diamine, cyclohexane dimethanol, resorcinol, bisphenol A, glycerol, trimethylolpropane, 1,2,6-hexanetriol, pentaerythritol, and combinations thereof.

Other suitable polyether polyols include polyether diols and triols, such as polyoxypropylene diols and triols and poly(oxyethylene-oxypropylene)diols and triols obtained by the simultaneous or sequential addition of ethylene and propylene oxides to di- or trifunctional initiators. Copolymers having oxyethylene contents of from about 5 to about 90% by weight, based on the weight of the polyol component, of which the polyols may be block copolymers, random/block copolymers or random copolymers, can also be used. Yet other suitable polyether polyols include polytetramethylene glycols obtained by the polymerization of tetrahydrofuran.

Suitable polyester polyols, for purposes of the present disclosure include, but are not limited to, hydroxyl-terminated reaction products of polyhydric alcohols, such as ethylene glycol, propylene glycol, diethylene glycol, 1,4-butanediol, neopentylglycol, 1,6-hexanediol, cyclohexane dimethanol, glycerol, trimethylolpropane, pentaerythritol or polyether polyols or mixtures of such polyhydric alcohols, and polycarboxylic acids, especially dicarboxylic acids or their ester-forming derivatives, for example succinic, glutaric and adipic acids or their dimethyl esters sebacic acid, phthalic anhydride, tetrachlorophthalic anhydride or dimethyl terephthalate or mixtures thereof. Polyester polyols obtained by the polymerization of lactones, e.g. caprolactone, in conjunction with a polyol, or of hydroxy carboxylic acids, e.g. hydroxy caproic acid, may also be used.

Suitable polyesteramides polyols, for purposes of the present disclosure, may be obtained by the inclusion of aminoalcohols such as ethanolamine in polyesterification mixtures. Suitable polythioether polyols, for purposes of the present disclosure, include products obtained by condensing thiodiglycol either alone, or with other glycols, alkylene oxides, dicarboxylic acids, formaldehyde, aminoalcohols or aminocarboxylic acids. Suitable polycarbonate polyols, for purposes of the present disclosure, include products obtained by reacting diols such as 1,3-propanediol, 1,4-butanediol, 1,6-hexanediol, diethylene glycol or tetraethylene glycol with diaryl carbonates, e.g. diphenyl carbonate, or with phosgene. Suitable polyacetal polyols, for purposes of the present disclosure, include those prepared by reacting glycols such as diethylene glycol, triethylene glycol or hexanediol with formaldehyde. Other suitable polyacetal polyols may also be prepared by polymerizing cyclic acetals. Suitable polyolefin polyols, for purposes of the present disclosure, include hydroxy-terminated butadiene homo- and copolymers and suitable polysiloxane polyols include polydimethylsiloxane diols and triols.

Specific examples of suitable supplemental polyols, for purposes of the present disclosure, are commercially available from BASF Corporation under the trademark of PLURACOL®, such as PLURACOL® GP Series polyols. A specific example of a suitable supplement polyol, for purposes of the present disclosure, is PLURACOL® GP430.

If employed, the supplemental polyol is typically present in the system in an amount of from about 1 to about 75, more typically from about 10 to about 50, and yet more typically about 40, parts by weight, each based on 100 parts by weight of the resin component of the system. It is to be appreciated that the system may include any combination of two or more of the aforementioned supplemental polyols.

The system may include one or more additional components, such as an additive component, in addition or alternate to the supplemental polyol. The additive component may comprise any conventional additive known in the art. Suitable additives, for purposes of the present disclosure include, but are not limited to, chain-extenders, cross-linkers, chain-terminators, processing additives, adhesion promoters, flame retardants, anti-oxidants, defoamers, antifoaming agents, water scavengers, molecular sieves, fumed silicas, ultraviolet light stabilizers, fillers, thixotropic agents, silicones, surfactants, catalysts, colorants, inert diluents, and combinations thereof. If employed, the additive component may be included in the system any amount, such as from about 0.05 to 10 parts by weight based on 100 parts by weight of the resin component of the system.

In certain embodiments, the additive component comprises an antifoaming agent. In one embodiment, the antifoaming agent comprises a silicone fluid including powdered silica dispersed therein. The silicone fluid can be employed to reduce and/or eliminate foaming of the binder. It should be appreciated that the silicone fluid may be predisposed in a solvent. Examples of antifoaming agents include Antifoam MSA and Antifoam A, commercially available from Dow Corning of Midland, Mich.

If employed, the antifoaming agent is typically present in the system in an amount of from about 0.01 to about 0.10, more typically from about 0.025 to about 0.075, and yet more typically about 0.05, parts by weight, each based on 100 parts by weight of the resin component of the system. It is to be appreciated that the system may include any combination of two or more of the aforementioned antifoaming agents.

In certain embodiments, the additive component comprises a molecular sieve. The molecular sieve is a hygroscopic agent that can be employed to maintain or increase desiccation, i.e., a state of dryness. The molecular sieve typically comprises molecules having a plethora of small pores. The small pores allow for molecules having a size smaller than the pores, such as water molecules, to be adsorbed while larger molecules, such as those present in the isocyanate and resin component, cannot be adsorbed. Typically, the molecular sieve can adsorb water up to and in excess of 20% of the weight of the molecular sieve. The molecular sieve, therefore, can act synergistically and in concert with the hydrophobic polyol to minimize the effect of water on the binder by adsorbing water before the water has a chance to react with the isocyanate component of the system.

If employed, it should be appreciated that any molecular sieve known in the art can be used, such as aluminosilicate minerals, clays, porous glasses, microporous charcoals, zeolites, active carbons, or synthetic compounds that have open structures through which small molecules, e.g. water, can diffuse. Examples of suitable molecular sieves include Baylith Paste and Molecular Sieve 3A, which are available from a variety of suppliers, such as Zeochem of Louisville, Ky.

If employed, the molecular sieve is typically present in the system in an amount of from about 0.01 to about 5.0, more typically from about 0.10 to about 2.0, and yet more typically about 0.50, parts by weight, each based on 100 parts by weight of the resin component of the system. It is to be appreciated that the system may include any combination of two or more of the aforementioned molecular sieves.

In certain embodiments, the additive component comprises fumed silica, which is commercially available from a variety of suppliers. An example of a suitable fumed silica is AEROSIL® R-972, commercially available from Evonic Industries Inc. of Essen, Germany. Fumed silica generally acts as a rheology control agent, and, if the fumed silica is hydrophobic, it imparts additional hydrophobicity to the binder.

If employed, the fumed silica is typically present in the system in an amount of from about 0.10 to about 10.0, more typically from about 1.0 to about 7.0, and yet more typically about 5.0, parts by weight, each based on 100 parts by weight of the resin component of the system. It is to be appreciated that the system may include any combination of two or more fumed silicas.

In certain embodiments, the additive component comprises a colorant. The colorant can be selected from the group of pigments, dyes, and combinations thereof. The colorant can be in either liquid or powder form. If employed, the colorant is typically a pigment or a pigment blend of two or more pigments. The pigment, or pigment blend, is used to impart a desired color to the binder and, if the pigment is inorganic, the pigment can also impart UV protection to the binder.

Different types of pigments can be used for purposes of the present disclosure. For example, titanium dioxide can be used to impart a white color and carbon black can be used to impart a black color, to the binder, respectively, while various blends of titanium dioxide and carbon black can be used to impart various shades of gray to the binder.

Examples of suitable grades of carbon black and titanium dioxide for purposes of the present disclosure are commercially available from Columbian Chemicals Company of Marietta, Ga., and DuPont® Titanium Technologies of Wilmington, Del., respectively. Other pigments including, but not limited to, red, green, blue, yellow, green, and brown, and pigment blends thereof, can also be used to impart color to the binder in addition to or alternative to carbon black and/or titanium dioxide.

More specific examples of colors, based on one or more colorants, include sapphire blue, jade green, Sedona red, amber brown, and topaz brown. Examples of suitable grades of pigments for purposes of the present disclosure are commercially available from various companies such as BASF Corporation and Penn Color, Inc. of Hatfield, Pa. It is to be appreciated that various blends of the aforementioned colorants, e.g. pigments, can be used to impart the binder with various colors, strengths, and shades.

If employed, the colorant is typically present in the system in an amount of from about 0.10 to about 5.0, more typically from about 1.0 to about 3.0, and yet more typically about 2.0, parts by weight, each based 100 parts by weight of the resin component of the system. It is to be appreciated that the system may include any combination of two or more of the aforementioned colorants.

In certain embodiments, the additive component comprises a catalyst component. In one embodiment, the catalyst component comprises a tin catalyst. Suitable tin catalysts, for purposes of the present disclosure, include tin(II) salts of organic carboxylic acids, e.g. tin(II) acetate, tin(II) octoate, tin(II) ethylhexanoate and tin(II) laurate. In one embodiment, the organometallic catalyst comprises dibutyltin dilaurate, which is a dialkyltin(IV) salt of an organic carboxylic acid. Specific examples of suitable organometallic catalyst, e.g. dibutyltin dilaurates, for purposes of the present disclosure, are commercially available from Air Products and Chemicals, Inc. of Allentown, Pa., under the trade name DABCO®. The organometallic catalyst can also comprise other dialkyltin(IV) salts of organic carboxylic acids, such as dibutyltin diacetate, dibutyltin maleate and dioctyltin diacetate.

Examples of other suitable catalysts, for purposes of the present disclosure, include amine-based catalysts, bismuth-based catalysts, nickel-base catalysts, zirconium-based catalysts, zinc-based catalysts, aluminum-based catalysts, lithium-based catalysts, iron(II) chloride; zinc chloride; lead octoate; tris(dialkylaminoalkyl)-s-hexahydrotriazines including tris(N,N-dimethylaminopropyl)-s-hexahydrotriazine; tetraalkylammonium hydroxides including tetramethylammonium hydroxide; alkali metal hydroxides including sodium hydroxide and potassium hydroxide; alkali metal alkoxides including sodium methoxide and potassium isopropoxide; and alkali metal salts of long-chain fatty acids having from 10 to 20 carbon atoms and/or lateral OH groups.

Further examples of other suitable catalysts, specifically trimerization catalysts, for purposes of the present disclosure, include N,N,N-dimethylaminopropylhexahydrotriazine, potassium, potassium acetate, N,N,N-trimethyl isopropyl amine/formate, and combinations thereof. A specific example of a suitable trimerization catalyst is commercially available from Air Products and Chemicals, Inc. under the trade name POLYCAT®.

Yet further examples of other suitable catalysts, specifically tertiary amine catalysts, for purposes of the present disclosure, include 1-methylimmidazol, DABCO 33-LV, dimethylaminoethanol, dimethylaminoethoxyethanol, triethylamine, N,N,N', N'-tetramethylethylenediamine, N,N-dimethylaminopropylamine, N,N,N',N', N"-pentamethyldipropylenetriamine, tris(dimethylaminopropyl)amine, N,N-dimethylpiperazine, tetramethylimino-bis(propylamine), dimethylbenzylamine, trimethylamine, triethanolamine, N,N-diethyl ethanolamine, N-methylpyrrolidone, N-methylmorpholine, N-ethylmorpholine, bis(2-dimethylamino-ethyl)ether, N,N-dimethylcyclohexylamine (DM-CHA), N,N,N',N', N"-pentamethyldiethylenetriamine, 1,2-dimethylimidazole, 3-(dimethylamino) propylimidazole, and combinations thereof. Specific examples of suitable tertiary amine catalysts are commercially available from Air Products and Chemicals, Inc. under the trade name POLY-CAT®, e.g. POLYCAT® 41.

If employed, the catalyst component can be employed in various amounts. Typically, the catalyst component is used in an amount to ensure adequate open/working time. It is to be appreciated that the catalyst component may include any combination of the aforementioned catalysts.

The system may be supplied to consumers for use by various means, such as in railcars, tankers, large sized drums and containers or smaller sized drums, kits and packets. For example, one kit can contain the isocyanate component and another kit can contain the resin component. Providing the components of the system to consumers separately provides for increased formulation flexibility of the binders formed therefrom. For example, a consumer can select a specific isocyanate component and a specific resin component, and/or amounts thereof, to prepare an binder.

The isocyanate and resin components typically have excellent storage stability or "free" stability. As such, the isocyanate and resin components can be separately stored (as the system) for extended periods of time before combining them to form the binder. It is to be appreciated that the system can comprise two or more different isocyanate components and/or two or more different resin components, which can be employed to prepare the binder. It is also to be appreciated that other components (e.g. the supplemental polyol, the additive component, etc.), if employed, can be supplied in the aforementioned isocyanate and/or resin components, or supplied as distinct components.

The present disclosure further provides an aggregate with the binder. The binder is generally formed from the isocyanate and resin components, as described and exemplified above. As introduced above, in certain embodiments, the isocyanate component comprises the polymeric isocyanate, and optionally, the isocyanate-prepolymer. In other embodiments, the isocyanate component comprises the polymeric isocyanate and the isocyanate-prepolymer. The isocyanate-reactive component comprises the hydrophobic polyol and the chain extender.

The amount of binder present in the weight coating generally depends on the particle size of the aggregate. Typically, the larger the aggregate particle size, the less binder is required to form the weight coating, and the smaller the aggregate size, the more binder is required to form the weight coating. Smaller sized aggregate generally requires more binder because there is more surface area to coat relative to larger sized aggregate. The binder is typically present in the weight coating in an amount of from about 1.0 to about 10.0, more typically from about 2.5 to about 5.0, and yet more typically about 4, parts by weight, each based on 100 parts by weight of the aggregate.

As used herein, the term aggregate is to be interpreted as referring to aggregate or aggregates in general and not to a single aggregate, nor is it to be construed to require more than one aggregate. Additionally, the term aggregate, as used herein, is intended to encompass a broad category of materials that serves as reinforcement, such as rock, gravel, fragmented stone, iron filings, sand, cement, and/or other mineral fillers. The term rock, as used herein, is intended to encompass all forms of rock, including, but not limited to, gravel, sand, etc. Additionally, the term rock as used herein is intended to encompass all species of rock, such as granite, limestone, marble, etc.

In certain embodiments, the aggregate comprises rock. It is to be appreciated that any type of rock can be used. The rock is typically selected from the group of granite, limestone, marble, beach stone, river rock, and combinations thereof. In a specific embodiment, the rock is granite.

The rock is typically present in the aggregate in an amount of from about 1 to about 100, more typically from about 50 to about 100, yet more typically from about 90 to about 100, and yet even more typically about 100, parts by weight, each based on 100 parts by weight of the aggregate in the weight coating. The remainder of the aggregate, if any, can be another different aggregate, such as sand, gravel, etc.

The average diameter of the rock is typically from about 0.001 to about 7.0, more typically from about 0.10 to about 5.0, yet more typically from about 0.25 to about 5.0, and yet even more typically from about 0.5 to about 3.0, inches. In other embodiments, the rock may be larger or smaller in size.

It is to be appreciated that the aggregate may include a combination of two or more of the aforementioned aggregates. For example, the aggregate of the weight coating can comprise mineral fillers and rock. In these embodiments, the mineral fillers are typically present in the aggregate an amount of from about 1.0 to about 99, more typically from about 25 to about 99, and yet more typically from about 75 to about 99, parts by weight, each based on 100 parts by weight of the aggregate present in the weight coating. Further, the rock is typically present in the aggregate in an amount of from about 99 to about 1.0, more typically from about 75 to about 1.0, and yet more typically from about 25 to 1.0, parts by weight, each based on 100 parts by weight of the aggregate present in the weight coating.

The aggregate can be supplied to consumers for use by various means, such as in railcars, tankers, large and small sized supersacks, large sized drums and containers or smaller sized drums, kits and packets. As described and exemplified above for description of the system, providing the components of weight coating to consumers separately provides for increased formulation flexibility of the weight coatings formed therefrom. For example, a consumer can select a specific aggregate, a specific isocyanate component, and a specific resin component, and/or amounts thereof, to prepare the weight coating.

Typically, the aggregate is dry (but for possible ambient humidity, if present), to prevent premature reaction with the isocyanate component of the system. In addition, it is believed that curing and bonding strength of the binder can be improved when the aggregate is dry. The aggregate can be kept dry by various methods, such as by using waterproof or water-resistant supersacks. However, in certain embodiments, the aggregate can at least be partially or completely submerged underwater, as described further below. It should also be appreciated that the aggregate may already be present in the location desired to include the weight coating, e.g. a railroad bed or along a coast line. As such, the aggregate may not need to be separately provided.

As described above, in certain embodiments, the binder comprises the reaction product of the isocyanate-prepolymer, the polymeric isocyanate, the hydrophobic polyol, and the chain extender. In other embodiments, the binder comprises the reaction product of an intermediate-prepolymer, the hydrophobic polyol, and the chain extender.

In the embodiments employing the intermediate-prepolymer, the intermediate-prepolymer is equivalent to the isocyanate component. Said another way, if employed, the intermediate-prepolymer takes place of the isocyanate component, and therefore, serves as the isocyanate component in such embodiments and descriptions thereof.

The intermediate-prepolymer typically comprises the reaction product of the isocyanate-prepolymer, the polymeric isocyanate, and the hydrophobic polyol. Optionally, the intermediate-prepolymer may comprise the further reaction product of the chain extender. Alternatively, the intermediate-prepolymer comprises the reaction product of the isocyanate-prepolymer, the polymeric isocyanate, and the chain extender. Optionally, the intermediate-prepolymer may comprise the further reaction product of the hydrophobic polyol.

Typically, the entire amount of the isocyanate-prepolymer and the polymeric isocyanate used to form the binder is employed to form the intermediate-prepolymer. In contrast, only a portion of the hydrophobic polyol and/or the chain extender is used to form the intermediate-prepolymer, while the remainder of the hydrophobic polyol and/or the chain extender is left for use as the resin composition.

In embodiments, the method for producing the weight coating system, comprises providing the isocyanate component and the isocyanate-reactive component; mixing the isocyanate component and the isocyanate-reactive component to form the polyurethane binder; applying the polyurethane binder to the aggregate to form the weight coating; and applying the weight coating onto the pipe. Preferred materials are described above. The process can in principle be carried out under reaction conditions known to those skilled in the art.

The examples below serve to illustrate the disclosure but are in no way limiting as regards the subject matter of the present disclosure.

EXAMPLES

A polyurethane binder according to the invention was prepared using a polyisocyanate (LUPRANATE® M20S), a branched polyether/polyester polyol (SOVERMOL® 1080), a second branched polyether/polyester polyol (SOVERMOL® 750), molecular sieve 3A, and antifoam A. The resin component included 75.85 pbw of branched polyether/polyester polyol (SOVERMOL® 1080), 4.1 pbw of the second branched polyether/polyester polyol (SOVERMOL® 750), 4.0 pbw of the Molecular Sieve 3A, and 0.05 of the Antifoam A. The polyurethane binder was prepared by mixing 150 g of the resin component and 66 g of the isocyanate component at 1800 rpm for 20 seconds.

The aggregate was prepared using ⅜ inch peastone that had been washed and oven dried. 160 g of the polyurethane binder was added to 4 kg of stones into a mixing drum to produce a weight coating.

In Example 1, a PVC pipe having a diameter of 58.74 mm (2.31 inches) was centered within a paper pipe having a diameter of 100 mm (3.94 inches), 15 inches of the weight coating described above was deposited around the pipe.

In Example 2, a metal pipe having a diameter of 34.93 mm (1.38 inches) was centered within a paper pipe having a diameter of 100 mm (3.94 inches). 11 inches of the weight coating was deposited around the pipe.

The weight coating system allows for longer lengths of pipe to be produced, welded, and subsequently reeled, thereby minimizing the amount of field joint work required and increasing the speed of installation. The weight coating system also has improved qualities including increased curability rates and increased flexibility.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present disclosure, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present disclosure has been described herein in an illustrative manner, and it is to be understood that the terminology which has been used is intended to be in the nature of words of description rather than of limitation. Many modifications and variations of the present disclosure are possible in light of the above teachings. The present disclosure may be practiced otherwise than as specifically described within the scope of the appended claims. The subject matter of all combinations of independent and dependent claims, both single and multiple dependent, is herein expressly contemplated.

What is claimed is:

1. A weight coating system, comprising:
   a pipe;
   a weight coating disposed around the pipe comprising an aggregate and a polyurethane binder,
   wherein the polyurethane binder is a two-component composition comprising an isocyanate component and an isocyanate-reactive component, and
   wherein the weight coating includes the polyurethane binder in an amount of from 1.0 to 10.0 parts by weight per 100 parts by weight of the aggregate.

2. The weight coating system according to claim 1, wherein the isocyanate-reactive component comprises a hydrophobic polyol.

3. The weight coating system according to claim 2, wherein the hydrophobic polyol comprises a natural oil polyol.

4. The weight coating system according to claim 3, wherein the natural oil polyol is castor oil.

5. The weight coating system according to claim 2, wherein the hydrophobic polyol comprises a polyether/polyester polyol.

6. The weight coating system according to claim 2, wherein the hydrophobic polyol comprises a polyether/polyester polyol, natural oil polyol, iron filings, sand, or other mineral fillers.

7. The weight coating system according to claim 6, wherein the natural oil polyol is castor oil.

8. The weight coating system according to claim 2, wherein the hydrophobic polyol is present in an amount of from about 80 to about 99 parts by weight based on 100 parts by weight of the isocyanate-reactive component.

9. The weight coating system according claim 1, wherein the isocyanate component comprises 4, 4'-diphenylmethane diisocyanate.

10. The weight coating system according to claim 1, wherein the isocyanate component has an NCO content of about 20-40 wt. % and an average NCO functionality of from about 1 to about 4.

11. The weight coating system according to claim 1, wherein the isocyanate component has an NCO content of about 25-35 wt. % and an average NCO functionality of from about 2 to about 3.

12. The weight coating system according to claim 1, wherein the isocyanate component has an NCO content of about 31.5 wt. % and an average NCO functionality of from about 2 to about 3.

13. The weight coating system according to claim 1, wherein the isocyanate-reactive component comprises a molecular sieve in an amount of from about 0.01 to about 5.0 parts by weight based on 100 parts by weight of said isocyanate-reactive component.

14. The weight coating system according to claim 1, wherein the isocyanate-reactive component comprises an antifoaming agent in an amount of from 0.01 to about 0.1 parts by weight based on 100 parts by weight of said isocyanate-reactive component.

15. The weight coating system according to claim 1, wherein the weight coating includes the polyurethane binder in an amount of from 2.5 to 5.0 parts by weight per 100 parts by weight of the aggregate.

16. The weight coating system according to claim 1, wherein the aggregate comprises rocks, gravel, fragmented stone, iron filings, sand, cement, and/or other mineral fillers.

17. A method for producing the weight coating system according to claim 1, comprising:
    providing the isocyanate component and the isocyanate-reactive component;
    mixing the isocyanate component and the isocyanate-reactive component to form the polyurethane binder;
    applying the polyurethane binder to the aggregate to form the weight coating; and
    applying the weight coating onto the pipe.

18. The weight coating system according to claim 1, wherein the weight coating system can be reeled and installed by a reel lay barge.

19. The weight coating system according to claim 1, wherein the weight coating system allows for longer lengths of pipe to be produced, welded, and subsequently reeled, thereby minimizing the amount of field joint work required and increasing the speed of installation.

20. The weight coating system according to claim 1, wherein the weight coating system has improved qualities including increased curability rates and increased flexibility.

* * * * *